United States Patent [19]

Marone

[11] Patent Number: 5,076,966
[45] Date of Patent: Dec. 31, 1991

[54] COMPOSITION AND METHOD FOR TESTING SMOKE DETECTORS

[75] Inventor: Joseph T. Marone, East Sandwich, Mass.

[73] Assignees: John J. McSheffrey, Hingham; Kevin L. McSheffrey, Duxbury, both of Mass.

[21] Appl. No.: 548,502

[22] Filed: Jul. 2, 1990

[51] Int. Cl.$^5$ .................................................. G01N 31/00
[52] U.S. Cl. .................................. 252/408.1; 73/31.05
[58] Field of Search .............. 252/305, 71, 73, 408.1; 73/31.05

[56] References Cited

U.S. PATENT DOCUMENTS

| | | | |
|---|---|---|---|
| 3,624,257 | 9/1971 | Sakai et al. | 260/327 M |
| 3,693,401 | 9/1972 | Purt et al. | 73/1 R |
| 3,876,631 | 4/1975 | Hawkins | 260/239.3 A |
| 3,876,758 | 4/1975 | Beekman | 424/47 |
| 3,891,663 | 6/1975 | Hawkins | 260/307 F |
| 3,968,208 | 7/1976 | Debourge et al. | 424/209 |
| 3,983,142 | 9/1976 | Hawkins | 260/348 C |
| 3,992,628 | 11/1976 | Karney | 250/338 |
| 4,301,674 | 9/1981 | Haines et al. | 73/1 |
| 4,462,244 | 7/1984 | Lee | 73/1 G |
| 4,473,565 | 9/1984 | Rovee et al. | 424/241 |
| 4,497,711 | 2/1985 | Shepherd | 210/656 |
| 4,578,193 | 3/1986 | Shepherd | 210/656 |
| 4,715,985 | 12/1987 | Pean et al. | 252/305 |
| 4,983,382 | 1/1991 | Wilmott et al. | 424/62 |
| 5,026,505 | 6/1991 | Tarnowski et al. | 562/43 |

Primary Examiner—Robert L. Stoll
Assistant Examiner—N. Bhat
Attorney, Agent, or Firm—Edward S. Roman

[57] ABSTRACT

A composition comprising a polyhydroxy alcohol and a water soluble solvent alcohol having a boiling temperature less than 100° C. and a method for dispensing the composition by way of an aerosol spray can is operative for testing smoke detectors of both the ionization and photoelectric type.

2 Claims, No Drawings

COMPOSITION AND METHOD FOR TESTING SMOKE DETECTORS

BACKGROUND OF THE INVENTION

1. Field of the Invention

This invention relates generally to a composition and method for testing smoke detectors of both the ionization and photoelectric type and, more particularly, to a composition and method for dispensing the composition by an aerosol spray can for testing smoke detectors of both types.

2. Brief Description of the Prior Art

There are two basic types of smoke detectors. One is an ionization detector which senses changes in the conductivity of the air in a measuring chamber or chambers under the influence of radioactive radiation. The other is a photoelectric detector which senses the scattering of light in a measuring chamber.

In an ionization type of detector, an electric field is set up between two electrodes by a DC voltage. When the air between the electrodes is ionized by the radioactive source, the resulting ions move under the effect of a field in the direction of the oppositely charged electrodes. Electric current results in a manner whereby the current strength depends on the number and velocity of the ions. When fire aerosols penetrate into the space between the two electrodes, a part of the ions is deposited onto the particles of these aerosols which are substantially heavier than the ions. The heavy ions move less freely as a result of the increase in mass inertia and thereby no longer contribute to the carrying of the charges thereby diminishing the current. The detector, in turn, senses the diminished current and sounds an alarm.

In the smoke detectors of the photoelectric type, there is provided a semiconductor diode which provides an infrared light source, the silicon cell operates as a light receiver, and a light absorber provides protection from light from sources outside the chamber. The diode emits light through pulses in the shape of a hollow cone; and, as long as the measuring chamber does not contain any smoke, the infrared light does not reach the receiver placed in the center axis of the light cone. When smoke penetrates the measuring chamber, smoke particles disperse the light rays in all directions and a part of the dispersed light reaches the photoelectric receiver which then produces an electric signal sounding the alarm.

As is well known, such smoke detectors are widely used as safety devices which are designed to protect lives and to reduce property damage by providing a warning of fire when the fire is in its earliest stage. How fast the smoke detector responds is of particular importance, since the time interval between the warning alarm and the spread of the fire through the building is a critical factor. A few minutes is often the difference between survival and death.

Detectors may fail to sound an alarm as quickly as required because their sensitivities can become altered over a period of time by dust, grease, corrosive fumes, moisture or by other contaminants in the area in which the detector is located. Electronic component failures are also known to occur as a result of aging, etc. Detector manufacturers typically provide for testing the device by means of pressing a test button or by pulling a switch which is located in the housing of the unit. Alternatively, some models can only be tested by blowing smoke in the direction of the detector through smoke derived from a cigarette, cigar, match, candle, paper, rope, etc.

There are major disadvantages in the conventional testing of smoke detectors. Since the recommended placement of smoke detectors is on the ceiling or high up on the wall, a person of average height must stand on a chair or on some elevation in order to press the button, pull the switch or blow the smoke, thus risking physical harm which could be a serious matter for older people. At best, blowing smoke is a clumsy and primitive method for testing such devices. Testing by way of a button or switch only assures that the alarm is operative and provides no indication as to whether the sensing chamber is operative.

One solution to this problem has been suggested in U.S. Pat. No. 4,301,674, entitled "Smoke Detector Tester", by W. Haines et al., issued Nov. 24, 1981, which shows a smoke detector tester comprising a handheld aerosol container for holding under pressure a quantity of spray emitted from the container by a finger valve in the form of an aerosol cloud within the sensing area of the smoke detector undergoing test. The contents of the aerosol spray can contain a hydrocarbon propellant, isopropyl alcohol and dioctyl phthalate which provides the particles in the aerosol detected by the smoke detector. The particles on the aerosol are provided by the dioctyl phthalate which can leave an oily residue. Other compositions that can be dispersed from aerosol cans for testing smoke detectors are suggested in U.S. Pat. No. 4,715,985, entitled "Composition for Checking the Functioning of Fire Detection Installations and Application to Various Types of Detectors", issued Dec. 29, 1987. The primary component suggested for these compositions is trichlorotrifluoroethane which may cause adverse environmental problems.

Therefore, it is a primary object of this invention to provide a composition for testing smoke detectors primarily by dispersion from an aerosol can in a manner that is economical, nontoxic and environmentally safe without leaving an oily residue.

SUMMARY OF THE INVENTION

A composition for checking the function in smoke detectors comprises a polyhydroxy alcohol and a water soluble alcohol having a boiling temperature lower than 100° C. The composition preferably contains about 0.5% to 50% by volume of polyhydroxy alcohol with the remaining portion comprising the low boiling point alcohol. The low boiling point alcohol is preferably selected from the group consisting of ethanol, methanol, 1-propanol, 2-propanol, 1-methyl-2-propanol, and 2-methyl-2-propanol. The composition may also include a suitable propellant gas to provide an aerosol spray. The propellant gas may be selected from the group consisting of isobutane, propane, butane, and chlorodifluoromethane (HCFC-22) or any suitable combination thereof. The aerosol composition suitable for dispersion from an aerosol can is preferably contained to have a vapor pressure within the range of 30 p.s.i. to 130 p.s.i.

DESCRIPTION OF THE INVENTION

The preferred composition of this invention for dispersal into a smoke detector to test the proper functioning thereof comprises a composition or solution of a polyhydroxy alcohol selected from the group consisting of ethylene glycol (1,2 ethanediol), propylene glycol (1,2-propanediol), trimethylene glycol (1,3-propanediol) and glycerol (1,2,3-propanetriol) mixed with an inexpensive water soluble alcohol solvent such as ethanol, methanol, 1-propanol, 2-propanol, 2-butanol, and 2-methyl-2-propanol having a boiling temperature lower than 100° C. The solution of polyhydroxy alcohol and the low boiling point solvent alcohol is inexpensive, nontoxic, and environmentally safe. The aforementioned composition can be packaged under pressure in any well-known aerosol spray can with any well-known propellant such as isobutane, propane, butane, and chlorodifluoromethane (HCFC-22) or any well-known suitable combination of these propellants.

Various compositions of glycerol comprising 1%, 2%, 5%, 10%, 20% and 50% of glycerol by volume dissolved respectfully in methanol, were prepared and operated to successfully test smoke detectors of both the ionization and photoelectric type. Also, a 0.5%, 1%, 5% and a 10% solution by volume of glycerol and ethanol was also prepared and operated to successfully test both the ionization and photoelectric type of smoke detectors. Ethanol would be the preferred solvent to methanol since it is entirely nontoxic.

Dispersal of the alcohol (preferably ethanol) glycerol composition of this invention from an aerosol spray can using one of the aforementioned propellants operates to disperse a wide range of droplet sizes in the air. The alcohol molecules such as ethanol tend to evaporate at a much faster rate than the glycerol molecules due to the lower boiling temperature of ethanol which boils at 78° C. versus the boiling temperature of glycerol which boils at 290° C. Thus, the intermolecular forces holding the glycerol molecules together in the liquid state are much greater than in ethanol where the hydrogen bonds are weaker. This results from the glycerol having three alcohol functional groups available for hydrogen bonding whereas the ethanol has only one active site for hydrogen bonding between molecules.

Thus, upon dispersal of the glycerol ethanol composition from an aerosol spray can there is formed a liquid aerosol in which thousands of glycerol molecules cluster together into droplets of sufficiently large size to be visible to the naked eye and capable of dispersing the light beam in the photoelectric smoke detector so as to set off the alarm in the aforementioned manner. Droplets are also sufficiently large enough so as to attract the attachment of ions in the ionization type of smoke detector thereby reducing the movement of ions sufficiently to set off the alarm. The ethanol, having a lower boiling point, completely evaporates into a gaseous state and has no observable effect on the smoke detectors. The pressure of the propellant gas in the aerosol spray can is preferably within the range of 30 p.s.i. to 130 p.s.i.

Other embodiments of the invention including other modifications of the preferred disclosed embodiments of the invention will be obvious to those skilled in the art and are within the scope of the following claims.

What is claimed is:

1. A method for checking the functioning of ionization or optical smoke detectors comprising the step of introducing into the vicinity of the detector a composition comprising a polyhydroxy alcohol and a water soluble solvent alcohol having a boiling temperature less than 100° C.

2. The method of claim 1 wherein the composition is introduced into the vicinity of the detector by spraying from an aerosol container having a suitable propellant gas thereon.

* * * * *